United States Patent [19]

Mortvedt

[11] Patent Number: 5,732,722
[45] Date of Patent: Mar. 31, 1998

[54] CAP FOR A TOOTHPASTE CONTAINER HAVING AN INCORPORATED SPOOL OF DENTAL FLOSS

[76] Inventor: David Michael Mortvedt, 14400 Hardee Chambliss Ct. #3, Centreville, Va. 20120

[21] Appl. No.: 799,001

[22] Filed: Feb. 7, 1997

[51] Int. Cl.[6] ................................................. A61C 15/04
[52] U.S. Cl. .................................... 132/325; 222/106
[58] Field of Search ............................. 132/323, 325, 132/324; 206/216, 63.5, 388; 222/192, 93, 106, 107

[56] References Cited

U.S. PATENT DOCUMENTS

| | | | |
|---|---|---|---|
| 1,614,260 | 1/1927 | Siewert | 222/93 |
| 1,733,114 | 10/1929 | Brennan | 132/321 |
| 3,586,212 | 6/1971 | Tzouras | 222/93 |
| 4,428,389 | 1/1984 | Cordero | 222/93 |
| 4,796,783 | 1/1989 | Paulson | 132/325 |

FOREIGN PATENT DOCUMENTS 9113594  9/1991  WIPO ............................ 132/322

*Primary Examiner*—Todd E. Manahan
*Assistant Examiner*—E. Robert

[57] ABSTRACT

A cap for a toothpaste container having an incorporated spool of dental floss including a toothpaste container coupling portion adapted for coupling with a dispensing outlet of a toothpaste container. A dental floss dispensing assembly is hingedly coupled with the toothpaste container coupling portion thereby keeping two essential components for dental hygiene together.

1 Claim, 3 Drawing Sheets

CAP FOR A TOOTHPASTE CONTAINER HAVING AN INCORPORATED SPOOL OF DENTAL FLOSS

BACKGROUND OF THE INVENTION

1. Field of the Invention

The present invention relates to a cap for a toothpaste container having an incorporated spool of dental floss and more particularly pertains to keeping two essential components for dental hygiene together with a cap for a toothpaste container having an incorporated spool of dental floss.

2. Description of the Prior Art

The use of dental floss dispensers is known in the prior art. More specifically, dental floss dispensers heretofore devised and utilized for the purpose of dispensing dental floss are known to consist basically of familiar, expected and obvious structural configurations, notwithstanding the myriad of designs encompassed by the crowded prior art which have been developed for the fulfillment of countless objectives and requirements.

By way of example, U.S. Pat. No. 5,076,302 to Chari discloses an apparatus for and method of dispensing dental floss.

U.S. Pat. No. 4,428,389 to Sanchez Cordero discloses a dental floss dispenser adapted to the cap of the common toothpaste.

U.S. Pat. No. Des. 336,782 to Vela et al. discloses a combined toothbrush, toothpaste dispenser and dental floss holder unit and cover therefor.

U.S. Pat. No. 4,957,125 to Yaneza discloses a toothbrushing assembly.

U.S. Pat. No. 4,919,156 to Gipson discloses a combination dental device.

U.S. Pat. No. 4,827,951 to Grussmark discloses a dental floss and toothpaste container.

While these devices fulfill their respective, particular objective and requirements, the aforementioned patents do not describe a cap for a toothpaste container having an incorporated spool of dental floss for keeping two essential components for dental hygiene together.

In this respect, the cap for a toothpaste container having an incorporated spool of dental floss according to the present invention substantially departs from the conventional concepts and designs of the prior art, and in doing so provides an apparatus primarily developed for the purpose of keeping two essential components for dental hygiene together.

Therefore, it can be appreciated that there exists a continuing need for new and improved cap for a toothpaste container having an incorporated spool of dental floss which can be used for keeping two essential components for dental hygiene together. In this regard, the present invention substantially fulfills this need.

SUMMARY OF THE INVENTION

In the view of the foregoing disadvantages inherent in the known types of dental floss dispensers now present in the prior art, the present invention provides an improved cap for a toothpaste container having an incorporated spool of dental floss. As such, the general purpose of the present invention, which will be described subsequently in greater detail, is to provide a new and improved cap for a toothpaste container having an incorporated spool of dental floss and method which has all the advantages of the prior art and none of the disadvantages.

To attain this, the present invention essentially comprises a toothpaste container coupling portion adapted for coupling with a dispensing outlet of a toothpaste container. The toothpaste container coupling portion is comprised of a first cylindrical member having an open lower end, a closed upper end and a cylindrical side wall therebetween. The closed upper end has an aperture therethrough in a central portion thereof. The aperture has an internally threaded channel extending downwardly therefrom. The internally threaded channel couples with a threaded dispensing spout of the toothpaste container with the open lower end receiving an upper portion of the toothpaste container. A dental floss dispensing assembly is hingedly coupled with the toothpaste container coupling portion. The dental floss dispensing assembly is comprised of a second cylindrical member having dimensions essentially the same as the first cylindrical member. The second cylindrical member has an open lower end, a closed upper end an a cylindrical side wall therebetween. The closed upper end has a central extent extending downwardly from an interior surface thereof. A free end of the central extent has a recess formed therein. The central extent rotatably receives a spool of dental floss therearound. A containment plate snapidly engages the open lower end of the second cylindrical member for positioning over the spool of dental floss for containment of the spool therein. The dental floss has a free end extending outwardly of an aperture through the cylindrical side wall of the second cylindrical member. A cutting edge is disposed adjacent to the aperture. A hinged door selectively covers the aperture and the cutting edge. The cylindrical side wall of the second cylindrical member has a notch formed therein downwardly of the closed upper end to facilitate lifting of the second cylindrical member away from the first cylindrical member.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved cap for a toothpaste container having an incorporated spool of dental floss which has all the advantages of the prior art dental floss dispensers and none of the disadvantages.

It is another object of the present invention to provide a new and improved cap for a toothpaste container having an incorporated spool of dental floss which may be easily and efficiently manufactured and marketed.

It is a further object of the present invention to provide a new and improved cap for a toothpaste container having an incorporated spool of dental floss which is of durable and reliable construction.

An even further object of the present invention is to provide a new and improved cap for a toothpaste container having an incorporated spool of dental floss which is susceptible of a low cost of manufacture with regard to both materials and labor, and which accordingly is then susceptible of low prices of sale to the consuming public, thereby making such a cap for a toothpaste container having an incorporated spool of dental floss economically available to the buying public.

Even still another object of the present invention is to provide a new and improved cap for a toothpaste container having an incorporated spool of dental floss for keeping two essential components for dental hygiene together.

Lastly, it is an object of the present invention to provide a new and improved cap for a toothpaste container having an incorporated spool of dental floss including a toothpaste container coupling portion adapted for coupling with a dispensing outlet of a toothpaste container. A dental floss dispensing assembly is hingedly coupled with the toothpaste container coupling portion thereby keeping two essential components for dental hygiene together.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts through the various Figures.

DESCRIPTION OF THE PREFERRED EMBODIMENT

Figure 1:
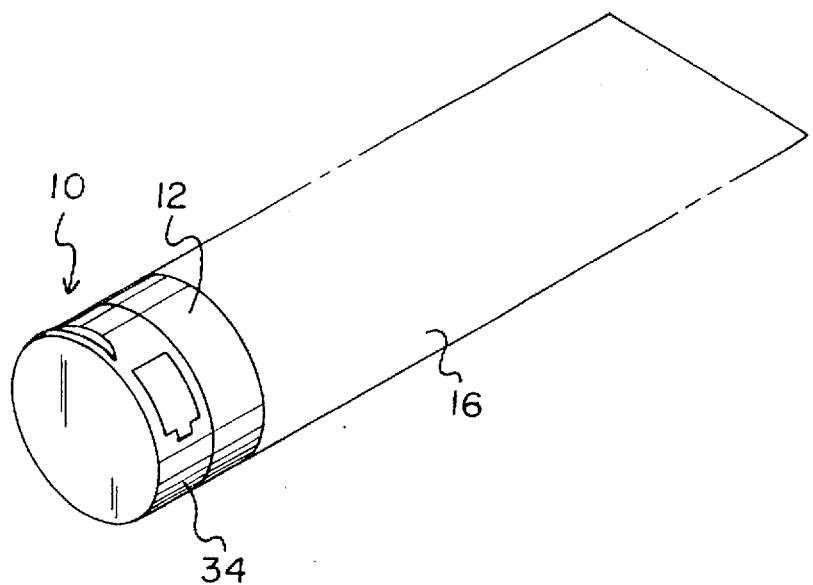
FIG. 1 is a perspective view of the preferred embodiment of the cap for a toothpaste container having an incorporated spool of dental floss constructed in accordance with the principles of the present invention.
Figure 2:
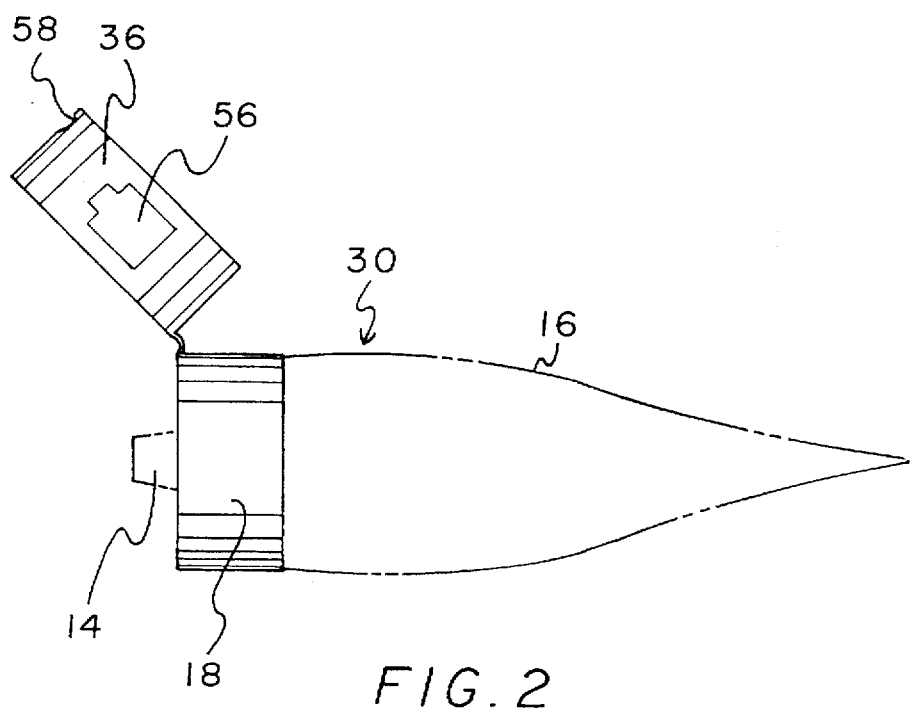
FIG. 2 is a side elevation view of the present invention illustrated coupled with a tube of toothpaste.
Figure 3:
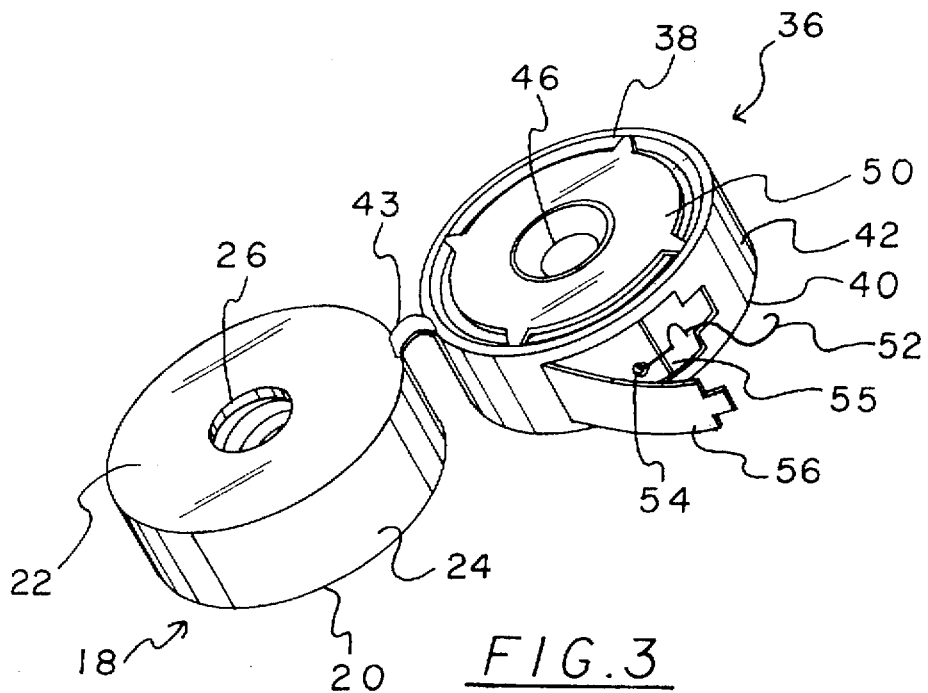
FIG. 3 is a perspective view of the present invention in an open orientation.

With reference now to the drawings, and in particular, to FIGS. 1 through 6 thereof, the preferred embodiment of the new and improved cap for a toothpaste container having an incorporated spool of dental floss embodying the principles and concepts of the present invention and generally designated by the reference number 10 will be described.

Specifically, it will be noted in the various Figures that the device relates to a cap for a toothpaste container having an incorporated spool of dental floss for keeping two essential components for dental hygiene together. In its broadest context, the device consists of a toothpaste container coupling portion and a dental floss dispensing assembly. Such components are individually configured and correlated with respect to each other so as to attain the desired objective.

The device 10 includes a toothpaste container coupling portion 12 adapted for coupling with a dispensing outlet 14 of a toothpaste container 16. Note FIGS. 1 and 2. The toothpaste container coupling portion 12 is comprised of a first cylindrical member 18 having an open lower end 20, a closed upper end 22 and a cylindrical side wall 24 therebetween. The closed upper end 22 has an aperture 26 therethrough in a central portion thereof. The aperture 26 has an internally threaded channel 28 extending downwardly therefrom. Note FIG. 5. The internally threaded channel 28 couples with a threaded dispensing spout of the toothpaste container 16 with the open lower end 20 receiving an upper portion 30 of the toothpaste container 16. Note FIGS. 1 and 2.

Figure 4:
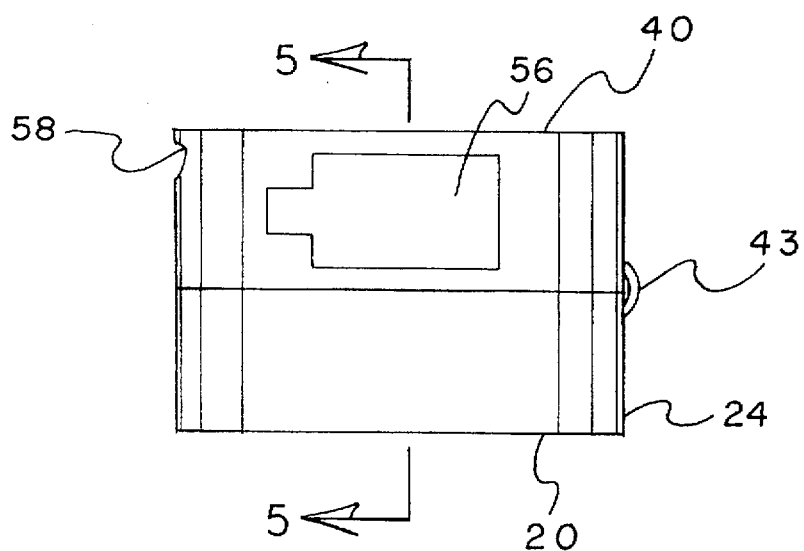
FIG. 4 is a side elevation view of the present invention.
Figure 5:
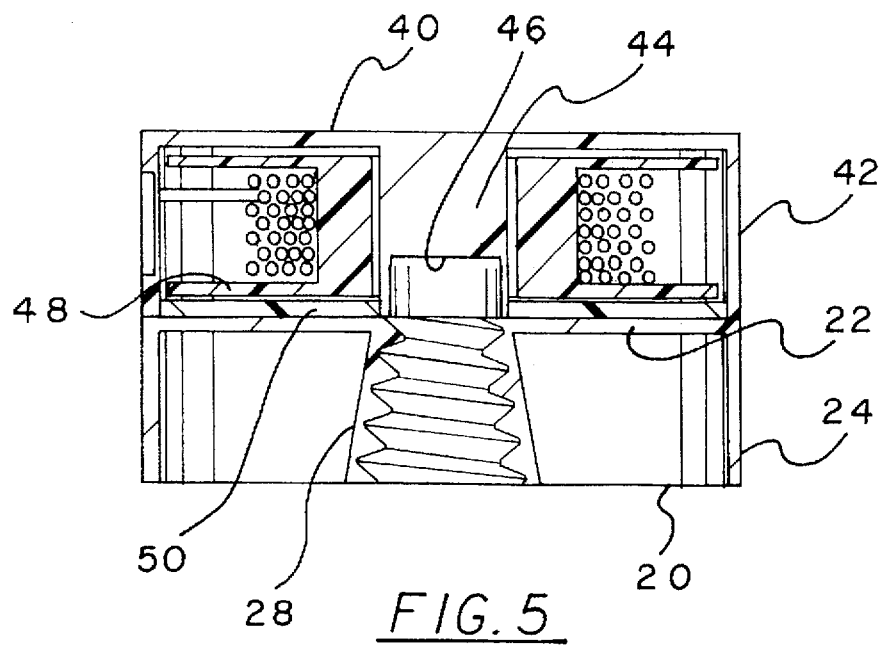
FIG. 5 is a cross-sectional view as taken along line 5—5 of FIG. 4.
Figure 6:
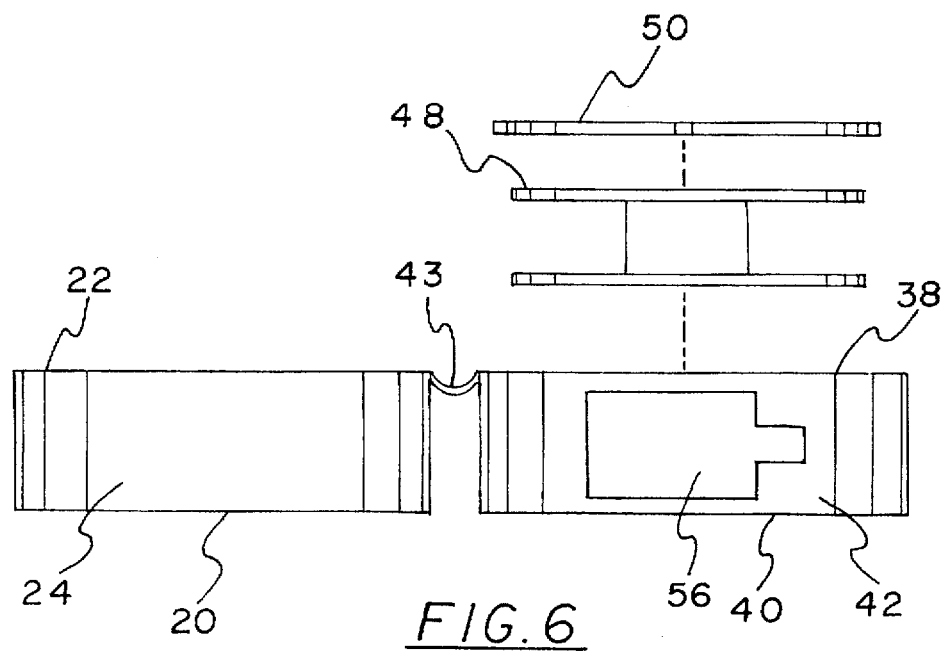
FIG. 6 is a side elevation view of the present invention illustrating the dental floss assembly.

A dental floss dispensing assembly 34 is hingedly coupled with the toothpaste container coupling portion 12. The dental floss dispensing assembly 34 is comprised of a second cylindrical member 36 having dimensions essentially the same as the first cylindrical member 18. The second cylindrical member 36 has an open lower end 38, a closed upper end 40 and a cylindrical side wall 42 therebetween. A flexible tab 43 extends between the first cylindrical member 18 and the second cylindrical member 36 to facilitate the hinged coupling therebetween. The closed upper end 40 has a central extent 44 extending downwardly from an interior surface thereof. A free end of the central extent 44 has a recess 46 formed therein. The recess 46 is positioned over the aperture 26 in the first cylindrical member when the device 10 is in the closed orientation as illustrated in FIGS. 4 and 5. The central extent 44 rotatably receives a spool 48 of dental floss therearound. A containment plate 50 snapidly engages the open lower end 38 of the second cylindrical member 36 for positioning over the spool 48 of dental floss for containment of the spool 48 therein. The containment plate 50 can be simply removed in order to replace the spool 48 of dental floss when needed. Note FIG. 6. The dental floss has a free end 52 extending outwardly of an aperture 54 through the cylindrical side wall 42 of the second cylindrical member 36. A cutting edge 55 is disposed adjacent to the aperture 54. A hinged door 56 selectively covers the aperture 54 and the cutting edge 55. The cylindrical side wall 42 of the second cylindrical member 36 has a notch 58 formed therein downwardly of the closed upper end 40 to facilitate lifting of the second cylindrical member 36 away from the first cylindrical member 18 to allow for toothpaste to be dispensed from the toothpaste container.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed as being new and desired to be protected by Letters Patent of the United States is as follows:

1. A cap having an incorporated spool of dental floss comprising, in combination:

a toothpaste container;

a toothpaste container coupling portion adapted for coupling with a dispensing outlet of a toothpaste container, the toothpaste container coupling portion comprising a first cylindrical member having an open lower end, a closed upper end and a cylindrical side wall therebetween, the closed upper end having an aperture therethrough in a central portion thereof, the aperture having an internally threaded channel extending downwardly therefrom, the internally threaded channel coupling with a threaded dispensing spout of the toothpaste container with the open lower end receiving an upper portion of the toothpaste container; and a dental floss dispensing assembly hingedly coupled with the toothpaste container coupling portion, the dental floss dispensing assembly comprising a second cylindrical member having dimensions essentially the same as the first cylindrical member, the second cylindrical member having an open lower end, a closed upper end and a cylindrical side wall therebetween, wherein a flexible tab extends between the first cylindrical member and the second cylindrical member, the closed upper end having a central extent extending downwardly from an interior surface thereof, a free end of the central extent having a recess formed therein and selectively situated over the aperture, the central extent rotatably receiving a spool of dental floss therearound, a containment plate removably and snappily engaging the open lower end of the second cylindrical member for positioning over the spool of dental floss for containment of the spool therein, the dental floss having a free end extending outwardly of an aperture through the cylindrical side wall of the second cylindrical member, a cutting edge disposed adjacent to the aperture, a hinged door selectively covering the aperture and the cutting edge, the cylindrical side wall of the second cylindrical member having a notch formed therein downwardly of the closed upper end to facilitate lifting of the second cylindrical member away from the first cylindrical member.

* * * * *